United States Patent [19]

Chen et al.

[11] Patent Number: 5,620,865

[45] Date of Patent: Apr. 15, 1997

[54] MEDIUM FOR DETECTING ENTEROCOCCI IN A SAMPLE

[75] Inventors: Chun-Ming Chen, Falmouth; Haoyi Gu, Portland, both of Me.

[73] Assignee: Idexx Laboratories, Inc., Westbrook, Me.

[21] Appl. No.: 335,149

[22] Filed: Nov. 4, 1994

[51] Int. Cl.$^6$ .............. C12Q 1/04; C12Q 1/10; C12Q 1/54; G01N 33/569

[52] U.S. Cl. ............. 435/34; 435/38; 435/7.34; 435/39; 435/29; 435/14; 435/7.2; 435/885

[58] Field of Search ............... 435/34, 38, 7.37, 435/39, 29, 14, 7.34, 7.2, 885

[56] References Cited

U.S. PATENT DOCUMENTS

| | | | |
|---|---|---|---|
| 3,206,317 | 9/1965 | Golber | 435/34 |
| 3,496,066 | 2/1970 | Berger | 435/34 |
| 4,235,964 | 11/1980 | Bochner | 435/34 |
| 4,259,442 | 3/1981 | Gayral | 435/34 |
| 4,591,554 | 5/1986 | Koumura et al. | 435/18 |
| 4,925,789 | 5/1990 | Edberg | 435/34 |
| 5,164,301 | 11/1992 | Thompson et al. | 435/34 |
| 5,464,755 | 11/1995 | Bochner | 435/34 |

FOREIGN PATENT DOCUMENTS

| | | |
|---|---|---|
| 0254771 | 2/1988 | European Pat. Off. . |
| 0261934 | 3/1988 | European Pat. Off. . |
| 2378858 | 8/1978 | France . |
| 9408043 | 4/1994 | WIPO . |

OTHER PUBLICATIONS

Gatti et al, Lett in Applied Microb, vol. 17, pp. 72–74, 1993.

Panosian and Edberg, "Rapid Identification of *Streptococcus bovis* by Using Combination Constitutive Enzyme Substrate Hydrolyses," *J. Clinical Microbiology* 27:1719–1722 (1989).

"Bacteriological Ambient Water Quality Criteria for Marine and Fresh Recreational Waters," *Ambient Water Quality Criteria for Bacteria*, USEPA (1986).

Cabelli, "Swimming–Associated Illness and Recreational Water Quality Criteria," *Wat. Sci. Tech.* 21:13–21 (1989).

Cabelli et al., "A marine recreational water quality criterion consistent with indicator concepts and risk analysis," *Journal WPCF* 55:1306–1314 (1983).

Damare et al., "Simplified Direct Plating Method for Enhanced Recovery of *Escherichia coli* on Food," *J. Food Science* 50:1736–1738 (1985).

de Man, "The Probability of Most Probable Numbers," *European J. Appl. Microbiol.* 1:67–78 (1975).

Donnelly and Hartman, "Gentamicin–Based Medium for the Isolation of Group D Streptococci and Application of the Medium to Water Analysis," *Applied And Environmental Microbiology* 35:5786–581 (1978).

Hernandez et al., "MPN Miniaturized Procedure for the Enumeration of Faecal Enterococci in Fresh and Marine Waters: The Must Procedure," *Wat. Res.* 27:597–606 (1993).

Kilian and Bulow, "Rapid Identification of Enterobacteriaceae," *Acta Path. Microbiol. Scand. Section B* 87:271–276 (1979).

Knutson and Hartman, "Comparison of Fluorescent Gentamicin–Thallous–Carbonate and KF Streptococcal Agars to Enumerate Enterococci and Fecal Streptococci in Meats," *Applied and Environmental Microbiology* 59:936–938 (1993).

Littel and Hartman, "Fluorogenic Selective and Differential Medium for Isolation of Fecal Streptococci," *Applied and Environmental Microbiology* 45:622–627 (1983).

Mooney et al., *Testing the Waters: A National Perspective on Beach Closings*, Natural Resources Defense Council, pp. 1–67 (1992).

Peeler et al, "Chapter 6—The Most Probable Number Technique," *Compendium of Methods for the Microbiological Examination of Foods*, 3rd ed., pp. 105–120, Vanderzant and Splittstoesser eds., American Public Health Association (1992).

*Standard Methods for the Examination of Water and Waste Water*, 18th ed., Greenberg et al. eds, pp. 9–45 to 9–63, 9–69 to 9–73 (1992).

Thomas, "Bacterial Densities From Fermentation Tube Tests," *J. Am. Water Works Assoc.* 34:572–576 (1942).

Trepta and Edberg, "Esculinase (β–glucosidase) for the rapid estimation of activity in bacerial utilizing a hydrolyzable substrate, p–nitrophenyl–β–D–glucopyranoside," *Antonie van Leeuwenhoek* 53:273–277 (1987).

*Primary Examiner*—John Kight
*Assistant Examiner*—Louise N. Leary
*Attorney, Agent, or Firm*—Lyon & Lyon

[57] ABSTRACT

Medium for growing Enterococci so that detection may be obtained within 24 hours.

16 Claims, No Drawings

MEDIUM FOR DETECTING ENTEROCOCCI IN A SAMPLE

FIELD OF THE INVENTION

This invention is in the field of chemistry, biology and microbiology and relates to novel means for detecting the presence of target microbes in a sample of a possibly contaminated material.

BACKGROUND

Microorganisms are present ubiquitously in biological specimens and environmental media suitable for their growth. However, some prove harmful to higher organisms and means for detecting their presence is important to preserve the public health. Many means for detecting various types of microorganisms are available offering various advantages with respect to speed and specificity.

All microorganisms have certain requirements for growth and reproduction. In general, microorganisms require the presence of the following for growth: an energy source including light and carbon compounds; and a source of raw materials including carbon, nitrogen, sulfur, and phosphorous as well as trace amounts of other minerals. Further, microorganisms must be present in a suitable environment wherein an appropriate temperature, pH, salinity and oxygen concentration is maintained.

A common procedure used to detect the presence of microorganisms involves adding a specimen to a culture medium containing all the necessary elements to allow growth. The sample may be natural or pretreated, as by membrane filtration, before being added to the culture medium, and the medium may or may not contain chemicals such as antimetabolites or antibiotics which are selectively active against microorganisms other than the target microorganism. Usually, these culture media have been sterile to assure no interference from contaminating microbes, and usually a rather long incubation step of from 48 to 72 hours has been required to provide for appropriate detection of Enterococci. Additionally, once growth is detected in these procedures, the target microorganism must be confirmed using one or more of a number of tests specific for a variety of physical and biochemical characteristics. These procedures are therefore labor intensive and time consuming.

Many efforts have been made to simplify and expedite the detection processes. Among these efforts have been attempts to measure specific by-products of individual bacteria, electrical impedance assays, ATP assays, and carbon-14 labelled substrate assays. Most have not proven highly efficacious. Also, indicators of microbial growth have been used which change color only after the microbe grows. They normally react chemically with a metabolic by-product produced by the target microbes. Chemicals which change color in the presence of pH changes associated with growth including phenol red, bromocresol blue, and neutral red have also been used. For instance, Golber, U.S. Pat. No. 3,206,317 uses phenol red in the presence of an acidic medium produced by bacterial waste products. Berger et al., U.S. Pat. No. 3,496,066 describes the use of compounds which bacteria convert to dyestuffs. Bochner, U.S. Pat. No. 4,129,483 describes using a non-biodegradable substance which is reduced to produce a color change. In all of these situations, the indicator is an additional substance and not one which also serves as a source of a required nutrient.

Edberg, U.S. Pat. No. 4,925,789 describes the use of a nutrient indicator which not only serves as a nutrient source, but also changes color upon being metabolized. The patent, herein incorporated by reference, provides a medium containing a nutrient indicator which, when metabolized by a target bacteria, releases a moiety which imparts a color or other detectable change to the medium. The procedure takes advantage of enzyme specificity unique to particular species or groups of bacteria. It suggests using antibiotics to select for growth of the microorganisms targeted and provides specific examples of liquid-based assays. Other methods previously used such as Kilian et al., *Acta. Path. Microbiol. Scand.* Sect. B §7 271–276 (1979) and Damare et al., *J. Food Science* 50:1736 (1985) report use of agar-based media without antibiotics.

Enterococcus density is a predictor of public health risks associated with contaminated recreation waters. There are two accepted methods for the analysis of Enterococcus density in water samples, the multiple-tube for most probable number technique (MPN) and the membrane filter technique (MF) (Greenberg et al., *Standard methods for the evaluation of water and wastewater* Eaton, A.D. (ed.) 18th ed. American Public Health Association (1992); and Mooney, K. et al., *Testing the waters: a national perspective on beach closings* Natural Resources Defense Council. (1992)). The results based on the multiple-tube technique may not be available for 72 hours, and the results of the membrane filter technique may not be available for 48 hours. The "MPN procedure" involves a 24 to 48 hour presumptive test in a series of azide dextrose broth followed by a 48 hour confirmation test using selective *Enterococcus agar* and 6.5% NaCl brain-heart infusion broth. The membrane filter technique involves the membrane filtration of water samples followed by incubation of a pre-filtered sterile membrane on Enterococcus selective media. The media of choice are either mE agar followed by an EIA substrate test, or *menterococcus agar*. Such methods may be tedious, labor intensive and time consuming. This may lead to delays in public notification and therefore increase public health risks.

SUMMARY OF THE INVENTION

The present invention features a medium which allows detection of Enterococci microbes in a liquified environmental or biological sample, within as little as 24 hours. The present medium is distinct from prior media in which about 48 to 72 hours are required to obtain a test result for Enterococci. The medium also allows quantifying the amount of Enterococci present in a sample and may be used in rapid screening methods.

The medium contains an effective amount of vitamin, amino acid, trace element and salt ingredients operable to allow viability and reproduction of Enterococci in the presence of a nutrient indicator. The nutrient indicator is provided in an amount sufficient to allow a detectable characteristic signal to be produced in the medium by the growth of Enterococci. The medium further contains effective amounts of selective agents which are active to prevent or inhibit the growth of non-target (i.e., non-enterococcal) microorganisms.

Media which have proven optimal in this invention for the detection of Enterococci in a sample include (per liter) a biological buffer (e.g., about 5.0 to 7.0 grams N-tris[Hydroxy-methyl]methyl-3-amino-propanesulfonic acid, free acid (TAPS-free acid), and about 5.0 to 7.0 grams N-tris[Hydroxy-methyl]methyl-3-amino-propanesulfonic acid, sodium salt (TAPS-sodium) or about 4.0 to 5.0 grams HEPES free acid and about 7.0 to 9.0 grams HEPES sodium salt)); and sodium bicarbonate (e.g., about 1.5 to 2.5 grams).

In addition, the following components are provided in the media in approximately the amounts indicated. Those in the art will understand that not every component is required. Components may also be substituted with other components of similar properties. The amounts of components may also be varied. Specifically, the medium contains (per liter) a total nitrogen content of about 1.0 to 1.7 grams (primarily from ammonium sulfate). Amino acids required for growth of the microorganisms to be detected are also provided. Not all amino acids must be provided, and the relative amount of each can vary. Amino acids may be provided from a variety of sources. These can be provided from natural sources (e.g., extracts of whole organisms), as mixtures or in purified form. The natural mixtures may contain varying amounts of such amino acids and vitamins. For general guidance, specific amounts of such amino acids and vitamins are indicated below. These amounts are for guidance only and are not limiting in this invention. Those in the art will recognize that many different combinations of amino acids and vitamins can be used in media of this invention. The lists provided below exemplify just one such example. Normally, only amino acids which cannot be synthesized endogenously by the microorganisms to be detected must be provided. However, other amino acids may be provided without departing from the medium of the invention. Amino acid contents preferably include at least the following in approximately the following amounts (per liter): Alanine (0.015 to 0.055 grams), Arginine (0.01 to 0.04 grams), Aspartic Acid (0.04 to 0.10 grams), Cystine (0.001 to 0.005 grams), Glutamic Acid (0.05 to 0.15 grams), Glycine (0.01 to 0.03 grams), Histidine (0.010 to 0.06 grams), Isoleucine (0.01 to 0.10 grams), Leucine (0.03 to 0.08 grams), Lysine (0.03 to 0.07 grams), Methionine (0.01 to 0.04 grams), Phenylalanine (0.01 to 0.04 grams), Proline (0.02 to 0.08 grams), Serine (0.01 to 0.05 grams), Threonine ( 0.01 to 0.04 grams), Tryptophan (0.002 to 0.006 grams), Tyrosine (0.01 to 0.02 grams), and Valine (0.02 to 0.05 grams).

Salts may be provided as a source of ions upon dissociation. Such salts may include potassium phosphate (e.g., about 0.5 to 1.5 grams); copper sulfate (e.g., about 40 to 50 µg); ammonium sulfate (e.g., about 4.0 to 6.0 grams); potassium iodide (e.g., about 50.0 to 150.0 µg); ferric chloride (e.g., about 150.0 to 250.0 µg); manganese sulfate (e.g., about 300.0 to 500.0 µg); sodium molybdate (e.g., about 150.0 to 250.0 µg); zinc sulfate (e.g. about 300.0 to 500.0 µg); and sodium chloride (e.g. about 0.05 to 0.15 g). Other inorganic moieties may be included to aid in microbe growth. These include the following (to the extent not already provided in the above sources of various chemical entities and described in amounts per liter): Phosphorus (about 0.0005 g/l), Potassium (about 0.0004 g/l), Sodium (about 0.03 to 0.06 g/l), and trace amounts of Calcium, Magnesium, Aluminum, Barium, Chloride, Cobalt, Copper, Iron, Lead, Manganese, Sulfate, Sulfur, Tin and Zinc.

Vitamins required for growth and reproduction of the microorganism sought to be detected may also be provided. These can be provided in a pure form or as part of more complex media. Such vitamins may be present in approximately the following amounts (per gram of medium): Biotin (about 0.15 to 0.40 µg/l), Pantothenic Acid (about 45.0 to 65.0 µg/l), Pyridoxine (about 6.0 to 9.0 µg/l), Riboflavin (about 10.0 to 20.0 µg/l), Folic acid (about 5.00 to 10.00 µg/l), Thiamine (about 10.0 to 20.0 µg/l), Vitamin B12 (about 0.20 to 0.30 µg/l), and Niacin (about 15.0 to 25.0 µg/l).

Selective agents, and in particular antibiotics, which inhibit or prevent growth of non-target organisms may also be provided. Many selective agents may be provided, and the selective agents used depends upon the target microorganism. Preferably, the selective agents include one or more of the following in concentrations within the following ranges: amikacin sulfate (about 0.0045 to 0.0055 grams/liter), amphotericin B (about 0.00198 to 0.00242 grams/liter), and Bacitracin (about 0.000476 to 0.00794 grams/liter). Alternatively, thallium acetate, neomycin sulfate, cycloheximide, tetracycline, colistin, ansiomycin or clindamycin may be substituted.

Those in the art will recognize that carbon, nitrogen, trace elements, vitamins, amino acids and selective agents can be provided in many forms. Generally, it is preferred to have an amount of vitamins, amino acids and selective agents in the range of the amounts provided above, but those in the art will recognize that the actual properties of each ingredient may be varied so that reduction in the amount of one ingredient can be compensated by an increase in the amount of another. This is particularly relevant when the essential amino acids, trace elements or vitamins of the microorganism sought to be detected are known. Some ingredients may be provided in reduced amounts or deleted if they may be synthesized endogenously by the microorganism whose presence is to be determined.

The nutrient indicator is present in the medium in an amount which is sufficient to support growth of the target microbe until a detectable characteristic signal is produced in the medium during growth. Together, the vitamin, amino acid, trace element, salt and nutrient indicator ingredients allow sufficient growth of the organism so that a detectable change in the sample may be observed. The nutrient indicator alters a detectable characteristic of the sample only when it is metabolized by an organism. Preferably, it alters a detectable characteristic only when it is metabolized by the target microbe. Therefore, it may be used to confirm the presence or absence of the target microbe in the sample. It is preferable that the nutrient indicator be chosen so that it is cleaved to release the indicator portion only by the target microbe in the medium. That is, if other microbes present in the sample could cleave the nutrient indicator then the medium is formed such that such other microbes cannot substantially grow in the medium. In addition, while it is preferred that the nutrient indicator is the only source of the specific type of nutrient for the target microbe, the medium may contain other such sources, but in amounts that will not reduce the specificity of the medium. For example, the nutrient indicator may be the only source of carbon for this microorganism. Alternatively, other carbon sources may be present (e.g. amino acids) which are not preferentially used by the target microbe. If desired, some small amount of another carbon source may be present which might be preferentially used by the target microbe, but the amount provided is such as not to reduce the specificity of the medium without such a carbon source. Most preferably, the nutrient indicator is 4-methylumbelliferyl-β-D-glucopyranoside. Other nutrient indicators which may be used in the invention include the following: 5-bromo-4-chloro-3-indoxyl-β-D-glucopyranoside, o-nitrophenyl-β-D-glucopyranoside, p-nitrophenyl-β-D-glucopyranoside, resofuran-β-D-glucopyranoside, 6-bromo-2-naphthyl-D-glucopyranoside, Rose-β-D-glucopyranoside, VQM-Glc (2-{2-[4-(D-glucopyranosyloxy)-3-methoxyphenyl]vinyl)-1-methylquinolinium iodide, and VBzTM-Gluc(2-{2-[4-(-D-glucopyranosyloxy)3-methoxyphenyl]vinyl}-3-methylbenzothiazolium iodide.

The term "Enterococci" includes the following microorganisms: *Enterococcus avium, E. casseliflavus, E. cecorum, E. columbae, E. dispar, E. durans, E. faecalis, E. faecium, E. gallinarum, E. hirae, E. malodoratus, E. mundtii, E. psudoavium, E. raffinosus, E. saccharolyticus, E. seriolicida, E. solitarius,* and *E. sulfureus.* Among them, *E. avium, E. durans, E. faecalis, E. faecium, E. gallinarum,* and *E. hirae* are the strains of fecal origin. The term is not limited to mean any given number of these species and is not meant to exclude species which have yet to be discovered but may later be identified and included in this genus by those of skill in the art.

The term "fecal streptococci" includes species of the Streptococci bacteria present in the gastrointestinal tract of higher organisms. It includes such organisms as *S. faecalis, S. faecium, S. avium,* and *S. gallinarum. S. faecalis, S. faecium, S. avium,* and *S. gallinarum* are more commonly referred to as Enterococci and are included within that term herein.

The term "24 hours" means the time required for about 95% of the liquid samples containing only about one to ten Enterococci per 100 ml to display a detectable characteristic change. The temperature, amount and type of enzyme inducer present, amount of nutrients provided in the medium, and the relative health of the bacteria all affect the detection time. The amount of nutrients such as amino acids, vitamins and trace elements provided may affect growth rate of the target microbe and thus detection time. Thermally equilibrating the sample to an incubation temperature of about 35° C. after adding the medium may decrease the time required for detection. The amount of enzyme inducer may also decrease the time to detection. Enzyme inducers found in the medium are agents which act as an inducer of the enzyme which cleaves the nutrient indicator. The enzyme inducer may, for example, be a homolog to the nutrient indicator. Examples of such inducers are known in the art. The relative health of the microbe also affects the time required for detection. Adding such agents as pyruvate which may aid recovery of injured organisms may therefore speed detection. If large numbers of bacteria are present in the sample, more rapid detection is also possible. In this invention, the media provided allows detection of low amounts of target microbes (i.e. less than 10/100 ml) in the 24 hour time period, at least 95% of the time. Standard methods can be used to determine such ability.

The term "medium" means a solid, powder or liquid mixture which contains all or substantially all of the nutrients necessary to allow a microbe to grow and reproduce. This invention includes both media which are sterilized as well as media which are not sterile.

The term "liquified" means substantially in liquid form, though it is also meant to include pulverized or homogenized samples of solid substances having at least a 10% liquid content. The phrase is meant to exclude a gelled medium, such as is found with agar.

The terms "environmental" and "biological" mean taken from or coming from a substance capable of supporting one or more life forms including algae, yeast and bacteria. Examples include but are not limited to recreational waters, marine waters, drinking waters, sewage effluents, and food substances.

The term "inoculation" means at or near the time the liquified environmental or biological sample is mixed with the medium of this invention. It is meant to be the time at which the two substances are substantially mixed together.

The term "effective amount" is an amount within the range which allows or promotes growth and reproduction of a target microorganism. That is, an amount which allows microbes or other organisms to adapt to the medium, synthesize the necessary constituents for reproduction and subsequently reproduce. It is not meant to be specific and may vary depending upon such factors as sample size and concentration of microorganisms. Generally, the term indicates the amount required to detect less than 100 target microbes per 1 ml sample, most preferable less than 100 microbes per 100 ml sample, or even 1 microbe per 100 ml sample.

The terms "vitamins", "amino acids", "trace elements" and "salts" are meant to include all molecules, compounds and substances classified in each category by those of skill in the art whether organic or inorganic, and the categories are not intended to exclude any substance which may be necessary for or conducive to maintaining life.

The term "nutrient indicator" means a molecule or substance containing a moiety that is a source for an essential nutrient and a moiety which causes or produces an observable characteristic change in the medium or sample. A nutrient indicator includes nutrient sources attached to or conjugated with chromogens or fluorogens. Nutrient sources may provide essential vitamin, mineral, element or amino acid ingredients or carbon. Normally, as a microorganism progresses from the phase in which nutrients are accumulated for reproduction (lag phase) and into the phase during which reproduction actually occurs at a relatively rapid rate (log phase), nutrition requirements increase. Consequently, increased amounts of the nutrient indicator are metabolized and a detectable and characteristic change is produced. Preferably, the nutrient indicator includes a nutrient moiety and a chromogen or a flurogen. Chromogens include any moieties which produce a color change observable in the visible range. Fluorogens include any moieties which fluoresce upon exposure to an excitation light source. Examples include, but are not limited to, orthonitrophenyl, phenolphthalein, and 4-methylumbelliferone moieties. While the nutrient indicator may provide the sole source of an essential nutrient, other sources of such nutrients may be provided, so long as adequate selectivity and sensitivity of the medium is maintained.

The term "detectable characteristic signal" includes any change in a sample which may be detected by one or more of the human senses. The term includes such examples as a color change in the visible or non-visible wavelength ranges, a change in state such as between solid, liquid and gas, an emission of gas, or a change in odor.

The term "target microbe" means the microorganism whose presence or absence is sought to be detected. Preferably, it includes species of enterococci and fecal streptococci which can live in the gastrointestinal tract of higher organisms.

In a preferred embodiment, the nutrient indicator alters the color of the microbe-specific medium. The color change may be apparent in the visible wavelength range or it may be fluorescence which is apparent in a wavelength range visible after exposure to an excitation light source. This is accomplished by the cleavage of a chromogenic moiety or fluorescent moiety. A chromogenic moiety is a moiety which changes the color of the sample in the visible range when it is in an unconjugated form, that is no longer conjugated to or bound to a nutrient moiety. A fluorescent moiety is a moiety which changes the color of the sample in the non-visible range when it is in an unconjugated form, that is no longer conjugated to or bound to a nutrient moiety. Examples of chromogenic moieties that may be conjugated to a nutrient moiety include, but are not limited to orthonitrophenyl moieties which produce a yellow color when released from the nutrient indicator, and phenolphthalein moieties which produce a red color when released from the nutrient indicator. Examples of fluorescent moieties include, methylumbelliferyl moieties which become fluorescent at about 366 nm when released from the nutrient indicator, and bromo-chloro-indole moieties which become blue when released from the nutrient indicator. Most preferably, the medium uses the fluorescent moiety, 4-methylumbelliferyl-β-D-glucopyranoside.

Preferably, the medium also contains one or more selective agents such as antibiotics which prevent or inhibit microbes other than the target microbe from metabolizing the nutrient indicator. That is, preferably the medium contains agents which are specific for microbes other than Enterococci or fecal Streptococci and effectively prevent or inhibit growth of at least some of those microbes. The term is meant to include such agents as sodium azide, thallium acetate, nalidixic acid, neomycin sulfate, gentamicin sulfate, bile salt, sodium chloride, lycloheximide, tetracycline, colistin, ansiomycin, clindamycin, and polymycin B. Preferably, it includes amikacin sulfate (e.g. about 0.0045 to 0.0055 g/liter), amphotericin B (e.g. about 0.00198 to 0.00242 g/liter) and bacitracin (e.g. about 0.000476 to 0.000794 g/liter).

The term "microbe-specific medium" means a medium which allows substantial growth of only the target microbe. This includes media which contain one or more antibiotics specific for inhibiting growth of microorganisms other than the target microbe, and it includes media which alternatively or additionally contain one or more nutrient indicators which are preferably not metabolized by microorganisms other than the target microbe to any substantial degree. The term "substantial" as used in this context, means that the medium still allows specific (i.e., at least 95% or even 98% accurate) and sensitive (i.e., at least 95% or even 98% detection levels) detection of the target microbe, as measured by standard procedures.

In another preferred embodiment, the medium contains an agent which acts as an inducer of the enzyme which cleaves the nutrient indicator. This agent may, for example, be a homolog to the nutrient indicator. Such inducers include isopropyl-β-D-thiogalactoside (IPTG) which induces β-galactosidase activity and ethyl-β-D-thioglucoside which induces β-glucosidase activity.

Preferably, the medium allows detection of Enterococci (including fecal Streptococci) within 24 hours. The medium is also preferably in the form of a non-sterile, water soluble powder to allow easy addition to liquid samples.

In another aspect, the invention features a method for detecting the presence or absence of Enterococci and fecal Streptococci in a liquified sample by contacting the sample with the medium described above, incubating the sample and the medium mixture, and monitoring the sample and medium mixture to determine the presence or absence of the detectable characteristic signal. The incubation may be performed at a variety of temperatures, but preferably it is carried out between 35° C. and 45° C. Preferably, the detectable characteristic signal may be observed within 24 hours. The invention features providing samples preferably from a water source including fresh water, marine water, drinking water supplies or waste water.

Another feature of the invention is a method for detecting the presence or absence of a target microbe in an environmental or biological liquid sample, preferably including the step of warming the sample to incubation temperature in a liquid incubator after adding the microbe-specific medium. Most preferably, the incubation temperature is about 35° C. The term "liquid incubator" means a liquid warmed to a specified temperature or temperature range. This may include any form of water baths for instance. Such an incubator is advantageous over previously used air incubators, since the medium more quickly reaches an adequate incubation temperature.

In yet another aspect, the invention features a method for quantifying the amount or number of Enterococci present in a liquid sample by contacting a liquid sample with the medium described above, placing the liquid sample including the medium in containers, incubating the liquid sample and medium mixture, observing the quantity and quality of a detectable characteristic signal, and comparing the quantity and quality of a detectable characteristic signal with most probable number values. This quantifying process features comparing the quantity and quality of the characteristic which has been altered, preferably a color change, to most probable number values obtained from samples where the concentration and characteristic change have been correlated with samples for which Enterococci or bacteria concentration is known. See e.g., *Compendium of Methods for the Microbiological Examination of Foods* 3rd ed., Edited by Vanderzant and Splittstoesser, 1992. The most probable number technique allows estimation of bacterial concentrations that are below detectable limits of other methods.

In preferred embodiments, the invention uses the apparatus described by Naqui in U.S. patent application Ser. No. 08/201,110, filed Feb. 23, 1994, now U.S. Pat. No. 5,518,892, hereby incorporated by reference. The quantifying step involves providing a sample of an environmental or biological sample in a liquid form, placing or dispensing the sample into the sample holding bag described by Naqui, mixing the sample with a medium to allow and promote growth of viable bacteria, incubating the sample, detecting the quantity and quality of the color change, and comparing that quantity and quality with results obtained for a series of samples for which the concentration of bacteria was known. More preferably, the incubation step is carried out at 41° C. for a period of 24 hours using the medium described above.

The invention provides the optimal medium for determining the presence of Enterococci (including fecal Streptococci) microorganisms. Enterococci can be detected much earlier in this medium than in those currently available. Therefore, the results of testing are more rapidly available. Rapid results save both money and time in the laboratory. Speed also decreases the threat to the public health, allowing early alerts and remedial measures to deal with the presence of some microorganisms in such places as drinking water supplies and recreational waters. Further, the method of this invention generally does not require confirmatory tests since microorganism-specific nutrient indicators may be used. Additionally, the invention does not require using a sterile medium as many other methods require.

Other features and advantages of the invention will be apparent from the following description of the preferred embodiments thereof, and from the claims.

BRIEF DESCRIPTION OF THE PREFERRED EMBODIMENTS

In the following description, reference will be made to various methodologies known to those of skill in the chemical, biological and microbiological arts. Publications and other materials setting forth such known methodologies to which reference is made are incorporated herein by reference in their entireties as though set forth in full. The compositions, methods, and products of this invention are applicable to biological and environmental specimens, and are useful in the chemical, biological and microbiological arts for the detection of microorganisms.

Detecting Microorganisms based on enzyme specificity

Specific microorganisms derive their nutrients from an array of sources, however, some sources may be unique to a particular microorganism or group of microorganisms. Families, groups or species of microorganisms may share enzyme specificity for certain nutrients which is lacking in other microorganisms. By taking advantage of the metabolic characteristics of specific microorganisms, it is possible to test for their presence. Many enzymes have been identified which are specific to particular groups or species and others likely will be identified in the future.

The enterococcus group of bacteria contain a unique constitutive enzyme, β-glucosidase (Littel, et al., Appl. Environ. Microbiol. 45:622-627 (1983). It catalyzes the hydrolysis of appropriate chromogenic or fluorogenic substrates under appropriate selective environments resulting in a colored or fluorescent signal that can be detected either visually or spectrophotometrically. A specific β-glucosidase substrate may serve as the nutrient indicator in media designed to detect enterococci and provide a major source of carbon in the medium formulation. A number of nutrient indicator substrates are available. However, the substrate preferably used in detecting enterococci is the fluorogenic substrate, 4-methylumbelliferyl-β-D-glucopyranoside. When viable enterococcus bacteria are present in a sample, the nutrient indicator is metabolized thereby cleaving the indicator portion which, when cleaved, becomes fluorescent. The glucose moiety released is then utilized by enterococci bacteria to promote growth.

Enterococci

The enterococcus and fecal streptococcus group of bacteria is a valuable bacterial indicator for determining the extent of fecal contamination in recreational surface waters (Greenberg, et al., Standard Methods for the Examination of Water and Wastewater. 18th ed. Eaton, A.D. (ed.) American Public Health Association (1992)). The genus Enterococcus now contains 18 species: *Enterococcus avium, Enterococcus casseliflavus, Enterococcus cecorum, Enterococcus columbae, Enterococcus dispar, Enterococcus durans, Enterococcus faecalis, Enterococcus faecium, Enterococcus gallinarum, Enterococcus hirae, Enterococcus malodoratus, Enterococcus mundtii, Enterococcus pseudoavium, Enterococcus raffinosus, Enterococcus saccharolyticus, Enterococcus seriolicida, Enterococcus solitarius,* and *Enterococcus sulfureus.* Among them, *Enterococcus avium, Enterococcus durans, Enterococcus faecalis, Enterococcus faecium, Enterococcus gallinarum,* and *Enterococcus hirae* are the stains of fecal origin (Hernandez, et al., Wat. Res. 27:597-606 (1993)). These bacteria survive much longer than other indicators in marine environments. Enterococci are also resistant to sewage treatment, including chlorination, and thus are sensitive indicators of the survival of enteric pathogens and viruses in water samples. A direct correlation between the concentration of enterococci in marine waters and the risks of swimming-associated gastroenteritis has been demonstrated (Cabelli, Wat. Sci. Tech. 21:13-21 (1989); and Cabelli et al., Journal WPCF (1983)). It has been recommended by the United States Environmental Protection Agency (U.S. EPA) that the enterococci group of bacteria be used as the bacterial indicators for fresh and marine waters. Current safety guidelines for recreational waters based on enterococci density are 33 enterococci per 100 ml for fresh water and 35 enterococci per 100 ml for marine water, respectively.

Current standard techniques for measuring enterococcus densities in marine and fresh recreational waters are labor intensive and time consuming. The results based on MPN require a minimum of 72 hours and MF requires 48 hours. Although enterococci are more sensitive bacterial indicators for swimming-associated health risks, the time required for result interpretation has hampered its acceptance for adequate monitoring. The β-glucosidase based diagnostic system allows early detection of enterococcus species in water samples within 24 hours. Rapid results allow speedy responses by government to effect such measures as beach closings to protect public health.

Selectivity

In general, β-glucosidase activity is a specific characteristic for detecting enterococci and fecal streptococci. Other bacteria, however, also possess such enzyme activity. These include the genera of the family of Enterobacteriaceae (*Enterobacter aerogenes, E. colacae*) *Klebsiella pneumoniae, Serratia marcescens, Listeria monocytogenes,* and *Bacterioides fragilis.* Certain selective factors(s) may be used to inhibit the growth of such other β-glucosidase positive bacteria (i.e. those other than enterococcus species).

A medium selective for specific microorganisms may be produced by utilizing a combination of enzyme specificity and selective environments. For instance, in one medium of this invention, non-target microbes which do not possess β-glucosidase activity and cannot digest the nutrient indicator are suppressed. Heterotrophic bacteria or other non-target microbes that possess β-glucosidase are selectively suppressed during the test period by the combination of specifically formulated chemical/antibiotic reagents and other physical parameters (pH and temperature). Typical selective agents that can be used in the medium of this invention include sodium azide, thallium acetate, nalixidic acid, neomycin sulfate, gentamicin sulfate, bile salt, sodium chloride, and polymycin B (Hernandez et al., Wat. Res. 27:597-606 (1993); Knuntson, et al., Appl. Environ. Microbiol. 59:936-938 ((1993); and Littel et al., Appl. Environ. Microbiol. 45:622-627 (1983)).

The combination of enzyme specificity and antibiotic selectivity provides multiple hurdles which prevent the competing non-enterococcus microbes from being detected within the test period of 24 hours. This avoids the use of a single, highly toxic element which not only may inhibit the non-target microorganisms but also suppress the target microbes.

Nutrient Indicator

In Enterococci, β-glucosidase catalyzes the conversion of the fluorescent substrate, 4-methylumbelliferyl-β-D-glucopyranoside (MUD), to 4-methylumbelliferone and glucose. The flurophore, 4-methylumbelliferone, emits blue fluorescence when excited at 365 nm (which may be viewed by a UV 365 nm-lamp). The released sugar moiety, glucose, serves as a major carbon source to support growth of Enterocicci. An increased nutrient indicator level may provide better microbial growth and stronger fluorescence, however, high nutrient indicator levels may also cause cell cytotoxicity and a greater level of background fluorescence. 4-methylumbelliferyl-β-D-glucopyranoside (MUD) at a level of 25 mg/l does not inhibit the growth of enterococcus species.

Enzyme Inducers

Most glycolytic hydrolases (β-glucosidase, β-galactosidase, and β-glucuronidase) are inducible. The induction of β-galactosidase activity by isopropyl-β-D-thiogalactoside (IPTG) is a classic example. Ethyl-β-D-thioglucoside which functions in a similar fashion is a β-glucosidase inducer.

Growth Stimulators $NaHCO_3$ (2 g/liter), Tween-80 (0.75 ml/liter), and $KH_2PO_4$ (5 g/liter) stimulate growth of fecal streptococcus species isolated from waters (See, e.g. Lachica et al., *J. Appl. Bacteriol.* 31:151-156 (1968)). Other trace elements such as specific amino acid(s) (glutamic acid), vitamin(s) (lipoic acid), and nucleotide(s) (kinetin riboside) may all have growth promoting activities for enterococcus species.

One medium that has proven optimal for detecting Enterococci is described in Table 1.

TABLE 1

| INGREDIENT | SOURCE | AMOUNT | |
|---|---|---|---|
| COMPONENT I | | | |
| Nitrogen | Amino Nitrogen | 0.02 to 0.05 | g/l |
| Amino Acids | Alanine | 0.015 to 0.055 | g/l |
| | Arginine | 0.01 to 0.04 | g/l |
| | Aspartic Acid | 0.04 to 0.1 | g/l |
| | Cystine | 0.001 to 0.005 | g/l |
| | Glutamic Acid | 0.05 to 0.15 | g/l |
| | Glycine | 0.01 to 0.03 | g/l |
| | Histidine | 0.01 to 0.06 | g/l |
| | Isoleucine | 0.01 to 0.10 | g/l |
| | Leucine | 0.03 to 0.08 | g/l |
| | Lysine | 0.03 to 0.07 | g/l |
| | Methionine | 0.01 to 0.04 | g/l |
| | Phenylalanine | 0.01 to 0.04 | g/l |
| | Proline | 0.02 to 0.08 | g/l |
| | Serine | 0.01 to 0.05 | g/l |
| | Threonine | 0.01 to 0.04 | g/l |
| | Tryptophan | 0.002 to 0.006 | g/l |
| | Tyrosine | 0.01 to 0.02 | g/l |
| | Valine | 0.02 to 0.05 | g/l |
| Elements | Calcium | trace | |
| | Chloride | trace | |
| | Cobalt | trace | |
| | Copper | trace | |
| | Iron | trace | |
| | Lead | trace | |
| | Manganese | trace | |
| | Phosphate | 0.0005 to 0.005 | g/l |
| | Potassium | 0.0004 to 0.004 | g/l |
| | Sodium | 0.03 to 0.06 | g/l |
| | Sulfate | trace | |
| | Sulfur | trace | |
| | Tin | trace | |
| | Zinc | trace | |
| Vitamins | Biotin | 0.15 to 0.4 | µg/l |
| | Choline | 5.0 to 10.0 | µg/l |
| | Pyridoxine | 6.0 to 7.5 | µg/l |
| | Riboflavin | 10.0 to 20.0 | µg/l |
| | Thiamine | 20.0 to 20.0 | µg/l |
| | Vitamin B12 | 0.2 to 0.3 | µg/l |
| | Niacin | 15.0 to 25.0 | µg/l |
| | Pantothenic Acid | 45.0 to 65.0 | µg/l |

TABLE 1-continued

| INGREDIENT | SOURCE | AMOUNT |
|---|---|---|
| COMPONENT II | | |
| HEPES free acid | | 4.032–4.928 g/l |
| HEPES sodium salt | | 7.301–8.933 g/l |
| modified yeast nitrogen base | | 4.635–5.665 g/l |
| sodium bicarbonate | | 1.8–2.2 g/l |
| potassium phosphate | | 0.1–1.0 g/l |
| β-ETG (ethyl-β-D-thioglucoside) | | 0.009–0.011 g/l |
| MUD (4-methylumbelliferyl-β-D-glucopyranoside) | | 0.02–0.03 g/l |
| amikacin sulfate | | 0.0045–0.0055 g/l |
| amphotericin B | | 0.00198–0.00242 g/l |
| Bacitracin | | 0.000476–0.000794 g/l |

*Trace = less than 0.001 g/liter

Methods of Use

The medium of this invention can be used in three different formats. First, it may be used to detect the presence or absence of Enterococci. Second, it may be used to quantify the amount of Enterococci present in a sample. Third, it may be used in a screening format to relate the time for a positive test result with the concentration of Enterococci in a sample.

Presence/Absence

The procedure to detect the presence or absence of enterococcus species in water samples is described below.

1. First, collect one or more water samples using precalibrated sterile vessels. The sample volume can be in various amounts, including 100 ml, 10 ml, or 1 ml depending on the application. The medium of this invention can be added in powder form to the collected water sample. Alternatively, the medium can be present in powder form in the vessels prior to sample collection.

2. The sample vessels are then thermally equilibrated (that is brought to incubation temperature in a water bath) preferably either at 35° C. or 41° C.±1° C., preferably for 20 minutes.

3. A blue fluorescence is indicative of the presence of Enterococcus species in the water sample tested when 4-methylumbelliferyl-β-D-glucopyranoside is the nutrient indicator. The fluorescence can be read visually using a UV 365nm lamp. Alternatively, the signal can be monitored by a fluorescence spectrophotometer using an excitation wavelength of 365 nm and an emission wavelength of 440–450 nm.

A positive reaction can occur anytime within 24 hours if there are viable bacteria present in the sample. That is, about 95% of samples containing 10 cfu/100 ml will have exhibited a detectable characteristic change within 24 hours. The time for detection, ranging from about 12 to 24 hours, varies with the concentration and presence of different species or strains of enterococci.

Quantification

The same medium can be used for quantifying target molecules. The assay can be done with the regular 5 or 10 tubes MPN format or the 50 to 100 wells "Quantitray" MPN format (See, Naqui, U.S. patent application Ser. No. 08/201, 110 filed Feb. 23, 1994, now U.S. Pat No. 5,518,892). The procedure for quantifying enterococci using the medium of Table I is described below:

1. Collect a water sample using one or more precalibrated sterile vessels. The sample volume can be in various amounts, including 100 ml, 10 ml, or 1 ml depending on the application. The invention can be added in powder form to the collected water sample. Alternatively, the medium of this invention can be present in powder form in the vessel prior to sample collection.

2. The sample is then poured into a "Quantitray" and then heat sealed to created 50 or 100 MPN wells. Alternatively, sample aliquots can be distributed into 5 or 10 MPN tubes.

3. The sample vessels are incubated preferably at 35° C. or 41° C.±1° C.

4. The fluorescence can be read visually using a UV 365 nm lamp. A blue fluorescence is indicative of a positive reaction when 4-methylumbelliferyl-β-D-glucopyranoside is used as the nutrient indicator. The enterococcus density in water samples can be directly correlated with the number of positive wells of "Quantitray" or the number of positive tubes using the MPN calculation formula, MPN=Nln (N/N-X) where N represents the total number of tubes or wells tested and X represents the total number of positive tubes or wells. The maximum time for detection is 24 hours.

Rapid Screening

The medium described above can also be used for the application of pass/fail rapid screening. This format involves the use of a direct linear relationship between the enterococcus density in a tested water sample with the detection time of positive results. The procedure for rapid pass/fail screening test using the same formula is followed:

1. A water sample is collected using a precalibrated sterile vessels. The sample volume can be in varying amounts, including 100 ml, 10 ml, or 1 ml depending on the application. The medium of this invention can be added in powder form to the collected water sample. Alternatively, the medium of this invention can be present in powder form in the vessel prior to sample collection.

2. The sample vessels are incubated preferably at 35° C. or 41° C.±1° C.

3. The fluorescence can be read visually or fluorospectrophotometrically. A blue fluorescence is indicative of a positive reaction. The time for positive result is used as an indicator to determine whether the water sample tested is at the level of "Hazard", "Concern", or "Pass".

Experiment 1

This experiment was conducted to determine the nutrient indicator which provides the most rapid detection.

Materials and Methods

Enterococcus strains used were grown on TSAI blood agar platters. The following microorganisms were grown: *E. faecalis* ATCC 19433, ATCC 33012, ATCC 33186, ATCC 35550, ATCC 29212; *E. faecium* ATCC 19434, ATCC 35667; *E. durans* ATCC 6056, ATCC 11576, ATCC 19432; *E. avium* ATCC 14025, ATCC 35665; *E. gallinarium* ATCC 49573; *Streptococcus bovis* ATCC 9809, ATCC 35034; and *S. equinus* ATCC 9812. Cell suspensions were prepared by taking the cells from plates using a sterile cotton swab (prewetted) and resuspended in pH 7.5 50 mM HEPES buffer to a turbidity equivalent to MacFarland Standard. The following enzyme substrates were tested for sensitivity to β-glucosidase: o-nitrophenyl-β-D-glucopyranoside (ONPD) and 4-methylumbelliferone β-D-glucopyranoside (MUD).

Data showed 4-methylumbelliferyl β-D-glucopyranoside was the most sensitive substrate to Enterococcus β-glucosidase activity. This substrate, when excited at 315 μm (monitor with UV-lamp), gives blue florescence upon hydrolysis by β-glucosidase.

Experiment 2

A study was performed using the nutrient formula provided in Table 1. It allowed detection of Enterococci at 1–2 cfu/100 ml within 16 to 22 hours (see table below). Water samples were collected and added to the medium described above. The sample vessels were then incubated at 41° C.±1° C. The sample vessels were monitored for the appearance of a blue fluorescence. The results are shown below and indicate sensitive detection of Enterococci in a medium of this invention.

Detection of Enterococcus with a Prototype Enterococcus Test

| Strains | Inoculum | 16 hr. | 18 hr. | 20 hr. | 22 hr. |
| --- | --- | --- | --- | --- | --- |
| E. faecalis | 26 cfu;100 ml | + | + | + | + |
| ATCC 33186 | 2.6 cfu/100 ml | + | + | + | + |
| E. faecium | 15 cfu/100 ml | + | + | + | + |
| ATCC 35667 | 1.5 cfu/100 ml | + | + | + | + |
| E. avium | 20 cfu/100 ml | W | + | + | + |
| ATCC 35665 | 2 cfu/100 ml | − | + | + | + |
| E. durans | 11 cfu/100 ml | W | + | + | + |
| ATCC 6056 | 1.1 cfu/100 ml | − | − | W | + |

"+"-positive; "−"-negative; "W"-weak fluorescence.

Other embodiments are within the scope of the following claims.

We claim:

1. A medium for detecting the presence or absence of Enterococci in a liquified sample within 24 hours comprising:

a) an effective amount of vitamins, amino acids, trace elements and salts operable to allow viability and reproduction of Enterococci;

b) an effective amount of one or more nutrient indicators provided in an amount sufficient to provide a detectable characteristic signal in the medium during growth of said Enterococci; said nutrient indicator releasing a nutrient moiety in the presence of β-glucosidase; and c) an effective amount of one or more selective agents active to prevent or inhibit the growth of microorganisms other than Enterococci.

2. The medium of claim 1 wherein said nutrient indicator is metabolized to a moiety that serves as a nutrition source and a moiety that alters an observable characteristic of said medium.

3. The medium of claim 2 wherein said nutrient indicator alters the color of said medium in a visible wavelength range through the action of beta glucosidase activity.

4. The medium of claim 2 wherein said nutrient indicator alters the color of said medium in a non-visible wavelength range through the action of beta glucosidase activity.

5. The medium of claim 1 wherein said nutrient indicator is 4-methylumbelliferyl-β-D-glucopyranoside.

6. The medium of claim 1 comprising: a buffer, 4.0 to 6.0 g/liter ammonium sulfate, a source of carbon dioxide and phosphorus ions, an effective amount of a β-glucosidase inducer, an effective amount of a nutrient indicator, an effective amount of antibiotics to inhibit growth of fungi and gram positive and gram negative bacteria other than Enterococci, and sufficient amino acids, vitamins, trace elements and minerals to support growth of enterococci at a rate to allow detection within 24 hours.

7. The medium of claim 6 comprising: a buffer, 4.000 to 6.000 g/l modified yeast nitrogen base, 1.0 to 2.5 g/l sodium bicarbonate, 0.1 to 1.0 g/l potassium phosphate, 0.009 to 0.011 g/l β-ETG, 0.02 to 0.03 g/l MUD, 0.0045 to 0.0055 g/liter amikacin sulfate, 0.00198 to 0.00242 g/liter amphotericin B, and 0.00476 to 0.00794 g/liter bacitracin, and sufficient amino acids, vitamins, trace elements and minerals to support growth of enterococci at a rate to allow detection within 24 hours.

8. Method for detecting the presence or absence of Enterococci in a liquified sample comprising the steps of:
   a) contacting a liquid sample with the medium of claim 1;
   b) incubating said liquid sample and said medium; and
   c) monitoring said liquid sample to determine the presence of a detectable change in a physical characteristic.

9. The method of claim 8 wherein said monitoring step lasts a maximum of 24 hours.

10. The method of claim 8 wherein said liquid sample is taken from a fresh or marine water source.

11. The method of claim 8 wherein said liquid sample is taken from a waste water source.

12. The method of claim 8 wherein said liquid sample is taken from a drinking water source.

13. The method of claim 8 wherein said detectable physical characteristic change is a color change.

14. The method of claim 8 wherein said detectable physical characteristic change is a color change visible in the presence of an excitation light source.

15. The method of claim 8 wherein said incubation step is performed at 35° C. to 45° C.

16. Method for quantifying the amount or number of Enterococci present in a liquid sample comprising the steps of:
   a) contacting a liquid sample with the medium of claim 1;
   b) placing said liquid sample and said medium in containers;
   c) incubating said liquid sample and medium mixture;
   d) observing the quantity and quality of a detectable change in a physical characteristic; and
   e) comparing the quality and quantity of a detectable change in said physical characteristic to most probable number values.

* * * * *